United States Patent
McGlynn et al.

(10) Patent No.: US 7,256,310 B2
(45) Date of Patent: Aug. 14, 2007

(54) LEVALBUTEROL SALT

(75) Inventors: Paul McGlynn, Marlborough, MA (US); Roger Bakale, Shrewsbury, MA (US); Craig Sturge, Falmouth (CA)

(73) Assignee: Sepracor Inc., Marlborough, MA (US)

( * ) Notice: Subject to any disclaimer, the term of this patent is extended or adjusted under 35 U.S.C. 154(b) by 305 days.

(21) Appl. No.: 10/728,873

(22) Filed: Dec. 8, 2003

(65) Prior Publication Data

US 2004/0115136 A1 Jun. 17, 2004

Related U.S. Application Data

(60) Provisional application No. 60/432,195, filed on Dec. 10, 2002.

(51) Int. Cl.
*C07C 215/00* (2006.01)
*C07C 205/00* (2006.01)

(52) U.S. Cl. .................................. 564/355; 568/706

(58) Field of Classification Search ................ 564/305, 564/463, 355; 568/700, 704, 705, 715, 717, 568/763, 840
See application file for complete search history.

(56) References Cited

U.S. PATENT DOCUMENTS

| | | | |
|---|---|---|---|
| 3,644,353 A | 2/1972 | Lunts et al. | |
| 5,225,183 A | 7/1993 | Purewal et al. | |
| 5,399,765 A | 3/1995 | Gao et al. | |
| 5,545,745 A | 8/1996 | Gao et al. | |
| 6,416,743 B1 | 7/2002 | Fassberg et al. | |
| 6,451,289 B2 | 9/2002 | Wherry, III et al. | |
| 6,475,467 B1 * | 11/2002 | Keller et al. | 424/45 |
| 2004/0101483 A1 * | 5/2004 | Muller-Walz et al. | 424/46 |
| 2004/0202616 A1 * | 10/2004 | Keller et al. | 424/46 |

FOREIGN PATENT DOCUMENTS

| | | | |
|---|---|---|---|
| CN | 1382685 | * | 12/2002 |
| CN | 1382685 A | | 12/2002 |
| WO | WO 96/32099 | | 10/1996 |

OTHER PUBLICATIONS

Kirk-Othmer Encyclopedia of Chemical Technology Copyright © 2002 by John Wiley & Sons, Inc., pp. 95-147, Article Online Posting Date: Aug. 16, 2002.*
Rouhi, "The Right Stuff, from research and development to the clinic, getting drug crystals right is full of pitfalls", Chemical & Engineering News, Feb. 24, 2003, pp. 32-35.*
Berge et al., Journal of Pharmaceuticals 66(1) (1977).*

* cited by examiner

*Primary Examiner*—Karl Puttlitz
(74) *Attorney, Agent, or Firm*—Martin A. Hay

(57) ABSTRACT

Levalbuterol L-tartrate affords crystals possessing properties desirable for use in a metered dose inhaler.

29 Claims, No Drawings

LEVALBUTEROL SALT

CROSS-REFERENCE TO RELATED APPLICATIONS

This application claims the benefit of U.S. provisional patent application No. 60/432,195 filed on Dec. 10, 2002, the disclosure of which is incorporated by reference herein.

BACKGROUND OF THE INVENTION

Levalbuterol (also known as (R)-albuterol) is a beta agonist useful as a relaxant of smooth muscle tissue, for example in the treatment of bronchospasm in patients suffering from asthma or chronic obstructive pulmonary disease. It is commercially available as a salt, levalbuterol hydrochloride, in a solution formulation adapted for administration by inhalation using a nebuliser and is sold in the United States under the brand name XOPENEX™. A process for the preparation of levalbuterol hydrochloride is described in U.S. Pat. No. 5,545,745. It has been found that crystals of levalbuterol hydrochloride obtained by this process are plate-like in shape and possess properties generally undesirable in a product intended for administration using a metered dose inhaler.

It would be desirable to administer levalbuterol using a metered dose inhaler (MDI).

The particles of active ingredients for delivery into the lungs of patients using an MDI must meet some very demanding criteria. The patient must be able to receive reproducible doses of a safe and effective amount of the particles deep into the lungs. Thus, the particles of the active ingredient must be of a stable, microscopic size within an acceptable distribution range. In particular, they must be resistant to agglomeration into larger particle clusters, and must not change in size or morphology during storage under varying conditions of temperature and relative humidity or in the presence of formulation components, such as carriers or propellants. Preferably they should have an aerodynamically favorable shape, such as a fiber (Crowder T. M., et al., Pharmaceutical Research, Vol. 19. No. 3, March 2002).

SUMMARY OF THE INVENTION

The present invention provides levalbuterol L-tartrate, including levalbuterol L-tartrate specifically in crystalline form; a process for preparing levalbuterol L-tartrate in crystalline form; a pharmaceutical composition comprising levalbuterol L-tartrate, including levalbuterol L-tartrate specifically in crystalline form; a metered dose inhaler comprising a canister containing an aerosol formulation of levalbuterol L-tartrate in crystalline form; and a method of affecting bronchodilation in a patient using levalbuterol L-tartrate, including levalbuterol L-tartrate specifically in crystalline form.

DETAILED DESCRIPTION OF THE INVENTION

A novel salt of levalbuterol has now been found that can be obtained in a crystalline form possessing properties particularly desirable in a particulate product to be formulated for administration by inhalation.

According to one aspect, therefore, the present invention provides levalbuterol L-tartrate.

Levalbuterol L-tartrate is a hemitartrate; that is to say it contains half a mole of L-tartaric acid per mole of levalbuterol.

It has been found that levalbuterol L-tartrate can be obtained in the form of needle-like crystals that possess particularly advantageous properties. Thus, the crystals have been found to be relatively resistant to agglomeration when micronized and, unlike crystals of the hydrochloride salt, to possess excellent stability, both as bulk drug and in the presence of aerosol formulation components, such as ethanol. They therefore provide a means for delivering effective, reproducible doses of aerosolized levalbuterol from a metered dose or dry powder inhaler into the lungs of patients requiring treatment.

The crystals have been prepared from (R)-benzylalbuterol by the process described hereinafter in Example 1. It has been found that the selection of (R)-benzylalbuterol as the starting material for the process, and the particular process conditions selected all effect the quality and properties of the crystals formed. However, persons skilled in the art will appreciate that alternative processes may be devised for producing crystals having properties essentially equivalent to those of the product of Example 1.

According to another aspect therefore, the present invention provides levalbuterol L-tartrate in crystalline form.

The crystals obtained by the process of Example 1 have been found to be needles of approximate dimensions 10-50 microns in length and 0.2 to 4 microns in width (by microscopic examination), and to contain very low levels of residual substances. The ethanol content (from the crystallization solvent) was found to be about 0.5% by weight after drying.

Particles of active ingredients for administration by inhalation desirably have an aerodynamic diameter of from 1 to 10 microns, preferably from 1 to 5 microns. If necessary, the size of particles obtained by crystallization may conveniently be reduced by micronization.

According to another aspect, therefore, the present invention provides levalbuterol L-tartrate in micronized form.

It has been found that crystals containing a reduced (0.3%) ethanol content do not readily afford a stable particle size distribution after micronization.

According to another aspect, therefore, the present invention provides levalbuterol L-tartrate crystals containing at least 0.3%, for example at least 0.4% ethanol, such as from 0.4 to 0.7% ethanol, preferably from 0.4 to 0.5%.

Drug substances are generally administered to patients in pharmaceutical compositions.

According to another aspect, therefore, the present invention provides a pharmaceutical composition, which comprises levalbuterol L-tartrate as described herein, together with a pharmaceutically acceptable carrier.

The pharmaceutical composition according to the invention may be adapted for administration to patients by any convenient route, such as by oral, mucosal (e.g. nasal, sublingual, vaginal, buccal or rectal), parenteral or transdermal administration. It may be in the form of, for example, a solution, suspension, powder, tablet, aerosol formulation, lozenge, suppository, emulsion, hard or soft gelatin capsule or syrup. The levalbuterol tartrate may be dissolved in the carrier, diluted by the carrier or supported by the carrier. Thus the carrier may be a support for the levalbuterol tartrate, such as a capsule, sachet, paper or other pharmaceutical container.

Preferably, the pharmaceutical composition is an aerosol formulation adapted for administration using a metered dose inhaler, the aerosol formulation comprising levalbuterol L-tartrate in crystalline form and a propellant.

The propellant may be any suitable propellant used in aerosol formulations, for example, a hydrofluoroalkane (HFA), such as 1,1,1,2-tetrafluoroethane (HFA134) or 1,1,1,2,3,3,3-heptafluoropropane (HFA227). HFA134 is preferred. The propellant may comprise at least 90% by weight of the aerosol formulation.

The aerosol formulation may further comprise a surfactant. The surfactant serves to stabilize the levalbuterol L-tartrate in a suspension, and may also serve as a valve lubricant in the metered dose inhaler. It may be any suitable surfactant used in aerosol formulations. Examples of surfactants used in aerosol formulations are described in U.S. Pat. No. 5,225,183, which is hereby incorporated by reference. A preferred surfactant is oleic acid. The surfactant, when present, may generally be present in an amount of from 1:100 to 1:10 surfactant:levalbuterol L-tartrate, preferably about 1:20.

The aerosol formulation may further comprise a co-solvent. A function of the co-solvent in the aerosol formulation is to facilitate dissolution of the surfactant, which may have poor solubility in the propellant. It may be any suitable carrier used in aerosol formulations. A preferred co-solvent is ethanol, especially dehydrated ethanol. The content of ethanol may conveniently be up to 10% by weight of the aerosol formulation, such as from 2 to 6%.

Metered dose inhalers comprise a canister containing an aerosol formulation, a metering valve and a valve stem. In use, a patient depresses the valve stem and inhales, causing a dose of the formulation to be administered and taken into the patient's lungs.

According to a further aspect, therefore, the present invention provides a metered dose inhaler comprising a canister containing an aerosol formulation as described herein, a metering valve and a valve stem.

Preferably the interior surface of the canister is coated, for example with a protective polymer. The inhaler preferably has an aperture with a diameter in the range of from 0.25 to 0.58 mm, more preferably from 0.25 to 0.48 mm, such as from 0.30 to 0.36 mm.

In one embodiment, the present invention provides a metered dose inhaler containing an aerosol formulation substantially as described in Example 3 herein. The safety and efficacy of levalbuterol tartrate administered using such a metered dose inhaler has been evaluated in clinical trials in comparison with Proventil HFA™. Proventil HFA™ is the trade name of a product sold by Schering Corporation in the United States. It is a metered dose inhaler containing racemic albuterol sulfate (i.e. containing a 1:1 mixture of (R)-albuterol and (S)-albuterol). The results of the clinical trials showed that administration of 90 µg of levalbuterol tartrate afforded the same efficacy as 180 µg of racemic albuterol sulfate. However, surprisingly, levalbuterol tartrate was found to give 5-20% lower systemic exposure (blood levels) of (R)-albuterol in adults compared with albuterol sulfate, and 30-40% lower exposure in children (ages 4-11). Systemic exposure to (R)-albuterol is undesirable, because the compound causes side effects associated with its activity as a beta agonist, and these side effects increase with increasing systemic exposure. The side effects include changes in serum potassium levels, elevated glucose levels and cardiovascular effects, such as increased heart beat rate. Accordingly, it is believed that levalbuterol tartrate provides a particularly advantageous vehicle for delivering (R)-albuterol to patients, especially to children.

In another embodiment, the pharmaceutical composition is in the form of a dry powder suitable for inhalation or insufflation. The composition may comprise levalbuterol L-tartrate crystals alone (e.g. having an aerodynamic diameter of from 1 to 10 microns, preferably from 1 to 5 microns), or levalbuterol L-tartrate blended or spray dried together with a suitable pharmaceutically acceptable carrier. Suitable pharmaceutically acceptable carriers include, without limitation, solvates of one or more natural or synthetic carbohydrates, such as a monosaccharides, disaccharides, trisaccharides, oligosaccharides, polysaccharides, polyols, amino acids and proteins, and/or in the form of their pharmaceutically acceptable esters, acetals, or salts (where such derivatives exist). The carrier is preferably lactose, more preferably lactose monohydrate. The dry powder composition may be presented in unit dosage form in, for example, capsules or cartridges of e.g. gelatin, or blister packs from which the powder may be administered with the aid of an inhaler or insufflator. The dry powder composition may be presented in multi dose form metered with the aid of an inhaler or insufflator.

Conveniently, dry powder formulations are administered using multidose dry powder inhalers.

The present invention therefore also provides a multidose dry powder inhaler, comprising a dry powder reservoir containing a dry powder aerosol formulation of levalbuterol L-tartrate as described hereinabove, and a metering chamber.

According to another aspect, the present invention provides a process for the preparation of levalbuterol L-tartrate, which comprises combining a solution of levalbuterol with a solution of L-tartaric acid and recovering levalbuterol L-tartrate crystals.

Preferably the solvent in each solution comprises ethanol. The solvent may be, for example, ethanol denatured with 5% methanol.

When the solvent in each solution comprises ethanol, the solution of levalbuterol is preferably combined with the solution of L-tartaric acid at a temperature in the range of from 47 to 65° C., more preferably from 48 to 60° C., especially from 50 to 53° C. It has been found that crystals formed from ethanol at a temperature above 60° C. (after drying) have a low ethanol content (less than 0.3%), whereas those formed at a temperature below 47° C. (after drying) have a high ethanol content (greater than 0.5%). Conveniently the solution of L-tartaric acid is added to the solution of levalbuterol gradually, for example over a period of from 1 to 3 hours, while maintaining the temperature within the preferred range. The resultant mixture is then allowed to cool, then the crystals are recovered, spread out on a tray and dried under vacuum at a temperature of about 35 to 40° C. It has been found that crystals according to the invention exhibit good stability at elevated temperatures with regard to dimer formation when compared with crystals of the sulfate salt; the commercial salt of racemic albuterol being the sulfate.

Levalbuterol L-tartrate is a hemitartrate. Hence, in preparing the crystals, preferably one mole of levalbuterol should be combined with half a mole of L-tartaric acid. The concentration of levalbuterol in the solution of levalbuterol is preferably in the range of from 0.38 to 0.43 moles per liter, such as from 0.38 to 0.42 moles per liter. The concentration of L-tartaric acid in the solution of L-tartaric acid is preferably in the range of from 0.94 to 1.06 moles per liter, such as from 0.96 to 1.03 moles per liter.

The process conditions are preferably selected so as to provide crystals having a median length of 10 to 50 microns and a median width of 0.2 to 4 microns.

Preferably the levalbuterol L-tartrate has been prepared by hydrogenating R-benzylalbuterol in the presence of palladium on carbon. Crystals prepared starting from levalbuterol that has been prepared from R-benzylalbuterol in this way have been found to be of high purity.

In general, the hydrogenation may be performed at a temperature in the range of from 20 to 45° C., preferably from 30 to 35° C., such as from 33 to 37° C. A convenient solvent is ethanol (commercially available ethanol is ethanol denatured with 5% methanol). The hydrogenation is preferably conducted under conditions selected to effect conversion of at least 99.9% of the R-benzylalbuterol without over reduction of other functional groups. The palladium on charcoal used preferably contains up to 0.33 wt % palladium. The reaction mixture is stirred or agitated during the hydrogenation.

(R)-benzylalbuterol may be obtained by the process described in U.S. Pat. No. 5,545,745.

According to another aspect, the present invention provides a method of effecting bronchodilation in a patient in need of treatment, which comprises administering an effective amount of levalbuterol L-tartrate.

Preferably micronized crystals of levalbuterol L-tartrate are administered to the patient by inhalation using a metered dose inhaler.

The patient may be a human or a non-human mammal, such as a dog, cat, horse, cow, sheep or pig. Preferably, the patient is a human.

The amount of levalbuterol L-tartrate administered will depend upon many factors, such as the species, weight and age of the patient, and the severity of the condition to be treated. For example, a dose administered to a human using a metered dose inhaler may contain from 25 to 120 µg of levalbuterol (calculated as the free base), such as 45 or 90 µg.

According to another aspect, the present invention provides levalbuterol L-tartrate, for use in therapy.

According to yet another aspect, the present invention provides the use of levalbuterol L-tartrate in the manufacture of a medicament for use as a bronchodilator.

According to a still further aspect, the present invention provides a pharmaceutical composition comprising levalbuterol L-tartrate and a pharmaceutically acceptable carrier for use as a bronchodilator.

Although the foregoing invention has been described in some detail for purposes of illustration, it will be readily apparent to one skilled in the art that changes and modifications may be made without departing from the scope of the invention described herein.

The following Examples illustrate the invention.

EXAMPLE 1

Preparation of Levalbuterol L-Tartrate in Crystalline Form

In the following, ethanol refers to the commercially available solvent, which is ethanol denatured with 5% methanol.

L-tartaric acid (4.11 kg) and ethanol (21.9 kg) were charged to a first reactor. The contents of the reactor were then agitated at a temperature in the range of from 20 to 25° C. to form a clear solution. The solution was then kept until it was used.

(R)-Benzylalbuterol (18.0 kg) and 10% palladium on carbon (50% water wet, 60 g) were charged to a suitable pressure reactor. The atmosphere of the reactor was then evacuated and replaced three times with nitrogen to exclude air. Under vacuum, ethanol (48.1 kg) was added, with agitation of the contents of the reactor. The atmosphere of the reactor was again evacuated and replaced three times with nitrogen to exclude air. Then, the atmosphere was pressurized to 50 psig (3.4 bar) with nitrogen and vented. After venting, the atmosphere was pressurized to 50 psig (3.4 bar) with hydrogen, then vented, and then once again pressurized to 50 psig (3.4 bar) with hydrogen. The temperature was then adjusted into the range of from 33 to 37° C., and the mixture was then agitated in this temperature range. The progress of the reaction was monitored at approximately one hour intervals until the reaction was complete [after 4.5 hours, the content of (R)-benzylalbuterol was 0.09%].

The hydrogen was then vented from the pressure reactor, and the atmosphere in the reactor was pressurized with nitrogen to 50 psig (3.4 bar) and vented three times. The contents of the reactor were then cooled to a temperature in the range of from 19 to 25° C., and then filtered through a 3 µm and 0.3 µm in-line cartridge filter into a glass lined reactor. Ethanol (59.3 kg) was then added, affording an approximately 11% by weight solution of levalbuterol. The solution was then heated to a temperature in the range of from 47 to 53° C.

The contents of the first reactor (a solution of L-tartaric acid) were then filtered through a 3 µm polishing filter and charged to the glass-lined reactor containing the levalbuterol over a period of 120 minutes. During this time, a precipitate formed. The first reactor was then rinsed with ethanol (6.17 kg), and the contents charged to the glass-lined reactor containing the precipitate. The contents were then agitated at 47 to 53° C. for 63 minutes, then cooled linearly to 19 to 25° C. over 128 minutes.

Approximately one third of the contents of the reactor were separated using a centrifuge. The product was then washed with ethanol (13.2 kg) and then again with ethanol (12.5 kg). The wet product (9.99 kg) was then discharged from the centrifuge.

Approximately one half of the remaining contents of the reactor were separated using the centrifuge. The product was then washed with ethanol (13.4 kg) and then again with ethanol (12.4 kg). The wet product (10.29 kg) was then discharged from the centrifuge.

The remaining contents of the reactor were then separated using the centrifuge. The product was then washed with ethanol (12.8 kg) and then again with ethanol (12.6 kg). The wet product (9.86 kg) was then discharged from the centrifuge.

The combined wet product was then loaded into a vacuum tray dryer and was dried at 35-40° C. for 21 hours to afford 16.51 kg of levalbuterol L-tartrate as needle-like crystals containing 0.49% ethanol. The crystals generally had a length of about 10-50 microns, a width of about 0.2 to 4 microns and an aspect ratio of about 20:1.

EXAMPLE 2

Micronization of Levalbuterol L-Tartrate Crystals

Levalbuterol L-tartrate crystals obtainable by the process of Example 1 were de-lumped by manual screening. The screened material was then micronized using a 4-inch (10.16 cm) pancake-style fluid energy mill with a venturi pressure of 50 psi (3.45 bar) and a mill pressure of 100 psi (6.895 bar). The mill operator used a vibratory feeder to supply the unmicronized levalbuterol L-tartrate to the mill at a rate of 1.4±0.4 kg per hour.

The resultant product consisted of crystalline needles comprising smaller needles (0.5 to 3 µm in length) with aspect ratios between 3:1 and 10:1, longer needles (3 to 9 µm in length) with aspect ratios of approximately 15:1, and fine particle fragments of approximately 0.5 μm.

The needle-like form of the particles in the micronized product is a typical of particles in a micronized product, which are usually more uniformly spherical in character. Needle-like particles are desirable in a product intended for administration by inhalation, due to their aerodynamic properties.

EXAMPLE 3

Metered Dose Inhaler Formulations of Levalbuterol L-Tartrate Crystals

|  | Amount per Can | | Amount per Gram | |
| --- | --- | --- | --- | --- |
| Component | (45 μg/ actuation)* | (90 μg/ actuation)* | (45 μg/ actuation)* | (90 μg/ actuation)* |
| Levalbuterol L-tartrate | 15.6 mg | 31.3 mg | 1.04 mg | 2.08 mg |
| Oleic Acid NF | 0.7815 mg | 1.563 mg | 0.0521 mg | 0.104 mg |
| Dehydrated ethanol USP | 0.7140 g | 0.7140 g | 0.0476 g | 0.0475 g |
| HFA 134a | 14.28 g | 14.28 g | 0.951 g | 0.950 g |
| Total | 15.01 g | 15.03 g | 1.00 g | 1.00 g |

*The dose is expressed as levalbuterol free base.

The formulation is prepared following a conventional procedure, for example as described below.

A portion of the requisite amount of dehydrated ethanol (approximately 94%) is added to a suitable tared formulation vessel previously flushed with filtered nitrogen. Oleic acid is added to the formulation vessel containing the dehydrated ethanol with the aid of a dehydrated ethanol rinse as needed to ensure quantitative transfer. A base mixer (approximately 250 rpm) is started, and the batch is homogenized for about 1 minute. The vessel and contents are then chilled to about 2-6° C. The speed of the base mixer is then reduced to approximately 100 rpm and micronized levalbuterol L-tartrate is added carefully to the vessel. The base mixer is then returned to approximately 250 rpm and the batch is homogenized for about 10 minutes. The remainder of dehydrated ethanol is then added to the batch to reach the required weight, followed by stirring for about 10 minutes at about 250 rpm. The vessel and contents are then chilled (2-6° C.), and this temperature is maintained throughout the subsequent filling process.

The concentrate suspension (e.g. 0.730±0.022 grams per can) is then filled into aluminum canisters having an interior coating of HOBA8666 (a pigmented epoxy phenolic resin available from HOBA, Lacke und Farben GmbH, Postfach 115772407, D-72411, Bodelhausen, Germany), and a valve is applied. The valve is crimped into place with an appropriate collet crimper. HFA 134a is then pressure-filled through the valve (e.g. 14.28 grams per can) using a positive piston filler with a suitable adapter. All units are stored (valve down orientation) for three days, followed by weight checking to remove units with gross leakage.

The canister is loaded into a standard metered dose inhaler actuator available from Bespak Europe, King's Lynn, Norfolk, PE30 2JJ, United Kingdom, having an aperture with a diameter in the range of from 0.30 to 0.36 mm.

Stability Study

A stability study has been conducted on batches of 45 μg and 90 μg per actuation products prepared as described above. The results are as follows:
25° C./60% RH, valve orientation up
25° C./60% RH, valve orientation down
40° C./75% RH, valve orientation up
40° C./75% RH, valve orientation down
The results are tabulated below.

25/60 valve up

|  | TEST | | | |
| --- | --- | --- | --- | --- |
|  | INITIAL | 1-MONTH | 3-MONTH | 6-MONTH |
| Particle Size - Andersen Cascade Impactor MMAD (μm) (Average) | 1.9 | 2.0 | 2.0 | 1.9 |
| Particle Size - Andersen Cascade Impactor GSD (Average) | 1.7 | 1.7 | 1.7 | 1.6 |
| Particle Size - Andersen Cascade Impactor fpf (Average) | 31.6% | 34.5% | 32.5% | 34.1% |
| Emitted Dose Uniformity Average (RSD) | 41.1 mcg (5.0%) | 42.0 mcg (2.7%) | [1]46.1 mcg (3.1%) | [1]45.9 mcg (2.3%) |

25/60 valve down

|  | TEST | | | |
| --- | --- | --- | --- | --- |
|  | INITIAL | 1-MONTH | 3-MONTH | 6-MONTH |
| Particle Size - Andersen Cascade Impactor MMAD (μm) (Average) | 1.9 | 1.9 | 2.0 | 1.8 |
| Particle Size - Andersen Cascade Impactor GSD (Average) | 1.7 | 1.7 | 1.7 | 1.5 |
| Particle Size - Andersen Cascade Impactor fpf (Average) | 31.6% | 32.9% | 32.9% | 34.6% |
| Emitted Dose Uniformity Average (RSD) | 41.1 mcg (5.0%) | 42.2 mcg (4.7%) | [1]46.8 mcg (3.5%) | [1]47.1 mcg (3.5%) |

40/75 valve up

|  | TEST | | | |
| --- | --- | --- | --- | --- |
|  | INITIAL | 1-MONTH | 3-MONTH | 6-MONTH |
| Particle Size - Andersen Cascade | 1.9 | 2.0 | 2.0 | 1.9 |

-continued

| | TEST | | | |
|---|---|---|---|---|
| | INITIAL | 1-MONTH | 3-MONTH | 6-MONTH |
| Impactor MMAD (μm) (Average) | | | | |
| Particle Size - Andersen Cascade Impactor GSD (Average) | 1.7 | 1.8 | 1.7 | 1.6 |
| Particle Size - Andersen Cascade Impactor fpf (Average) | 31.6% | 31.6% | 32.8% | 34.3% |
| Emitted Dose Uniformity Average (RSD) | 41.1 mcg (5.0%) | 41.9 mcg (3.4%) | [1]47.3 mcg (3.3%) | [1]48.1 mcg (3.3%) |

40/75 valve down

| | TEST | | | |
|---|---|---|---|---|
| | INITIAL | 1-MONTH | 3-MONTH | 6-MONTH |
| Particle Size - Andersen Cascade Impactor MMAD (μm) (Average) | 1.9 | 2.1 | 2.1 | 2.0 |
| Particle Size - Andersen Cascade Impactor GSD (Average) | 1.7 | 1.8 | 1.6 | 1.6 |
| Particle Size - Andersen Cascade Impactor fpf (Average) | 31.6% | 31.6% | 33.5% | 33.7% |
| Emitted Dose Uniformity Average (RSD) | 41.1 mcg (5.0%) | 40.5 mcg (3.2%) | [1]48.0 mcg (3.3%) | [1]51.0 mcg (2.4%) |

[1]NB 3 month data set includes method change that improved collection efficiency.

Particle Size Definitions

Aerodynamic Diameter—The diameter of a unit-density sphere having the same terminal settling velocity as the particle in question. It is used to predict where in the respiratory tract such particles will deposit.

Aerodynamic (equivalent) diameter—diameter of a unit-density sphere having the same gravitational-settling velocity as the particle in question. 1 Aerodynamic diameter takes into account the shape, roughness, and aerodynamic drag of the particle. Used for movement of particles through a gas.

Cascade impactor—a device that uses a series of impaction stages with decreasing particle cut size so that particles can be separated into relatively narrow intervals of aerodynamic diameter; used for measuring the aerodynamic size distribution of an aerosol.

Geometric standard deviation—(GSD)— A measure of dispersion in a lognormal distribution (always greater than or equal to 1.0).

Mass median aerodynamic diameter—(MMAD)— The geometric mean aerodynamic diameter. Fifty percent of the particles by weight will be smaller that the MMAD, 50% will be larger.

Fine particle fraction—(fpf)—a proportion of the emitted dose collected on stages 3 to filter of an Anderson Cascade impactor.

Relative standard deviation—(RSD)

REFERENCES

1—Aerosol Measurement: Principles, Techniques and Applications. Edited by Klaus Willeke and Paul A. Baron. Van Nostrand Reinhold, N.Y., 1993.

2—Fundamentals of Aerosol Sampling. Gregory D. Wight. Lewis Publishers, CRC Press, 1994

Comparison of the Solubility of Levalbuterol L-Tartrate Crystals with that of Levalbuterol Hydrochloride Crystals in HFA 134/Ethanol Blends

| Active Salt | Actual Ethanol % | Day 1 μg/g | Day 2 μg/g | Day 4-5 μg/g | Day 6-8 μg/g | Day 57-65 μg/g |
|---|---|---|---|---|---|---|
| Tartrate | 0.00 | NA | 0.00 | | 0.02 | 0.12 |
| | 2.01 | 0.07 | 0.10 | | 0.44 | 1.18 |
| | 5.28 | 0.69 | 0.94 | | 1.81 | 2.97 |
| | 9.80 | 1.65 | 2.32 | | 5.30 | 6.82 |
| Hydrochloride | 0.00 | 0.08 | 1.13 | 0.33 | | 4.20 |
| | 2.16 | 4.45 | 5.01 | 5.25 | | 10.57 |
| | 5.25 | 30.93 | 31.89 | 36.54 | | 41.07 |
| | 10.16 | 127.78 | 132.92 | 134.15 | | 151.96 |

The results show that levalbuterol L-tartrate has substantially lower solubility in ethanol than levalbuterol hydrochloride. This property is desirable in crystals to be used in the preparation of an aerosol formulation adapted for use in a metered dose inhaler, because such formulations are commonly prepared by combining micronized crystals with ethanol (as a co-solvent), then adding the propellant (which would force any dissolved product back out of solution, potentially causing crystal growth).

The invention claimed is:
1. Levalbuterol L-tartrate.
2. Levalbuterol L-tartrate as claimed in claim 1, which is in crystalline form.
3. Levalbuterol L-tartrate as claimed in claim 2, containing from 0.3 to 0.7% ethanol.
4. Levalbuterol L-tartrate as claimed in claim 2, which is in micronized form.
5. Levalbuterol L-tartrate as claimed in claim 4, which is in the form of needle-like particles.
6. A pharmaceutical composition, which comprises levalbuterol L-tartrate as claimed in claim 1, together with a pharmaceutically acceptable carrier.
7. A pharmaceutical composition as claimed in claim 6, which is an aerosol formulation adapted for administration using a metered dose inhaler, the aerosol formulation comprising levalbuterol L-tartrate in crystalline form and a propellant.
8. A pharmaceutical composition as claimed in claim 7, in which the propellant is 1,1,1,2-tetrafluoroethane.
9. A pharmaceutical composition as claimed in claim 7, which further comprises a surfactant.
10. A pharmaceutical composition as claimed in claim 7, which further comprises a co-solvent.
11. A pharmaceutical composition as claimed in claim 10, in which the co-solvent is ethanol.
12. An aerosol formulation adapted for administration using a metered dose inhaler, the aerosol formulation com- prising levalbuterol L-tartrate crystals in the form of micronized, needle-like particles, and a propellant.

13. An aerosol formulation as claimed in claim 12, in which the propellant is 1,1,1,2-tetrafluoroethane.

14. An aerosol formulation as claimed in claim 13, which further comprises from 2 to 6% by weight of ethanol as a co-solvent.

15. A metered dose inhaler comprising a canister containing an aerosol formulation as defined in claim 7, a metering valve and a valve stem.

16. A metered dose inhaler comprising a canister containing an aerosol formulation as defined in claim 12, a metering valve and a valve stem.

17. A pharmaceutical composition as claimed in claim 6, which is adapted for administration using a dry powder inhaler or insufflator.

18. A process for the preparation of levalbuterol L-tartrate crystals, which comprises combining a solution of levalbuterol with a solution of L-tartaric acid and recovering levalbuterol L-tartrate crystals.

19. A process as claimed in claim 18, in which the solvent in each solution comprises ethanol.

20. A process as claimed in claim 18, in which the crystallization conditions are selected so as to provide crystals having a length of 10 to 50 microns and a width of 0.2 to 4 microns.

21. A process as claimed in claim 18, in which the levalbuterol has been prepared by hydrogenating R-benzylalbuterol in the presence of palladium on carbon.

22. A process as claimed in claim 21, in which the hydrogenation has been conducted under conditions selected to effect conversion of at least 99.9% of the R-benzylalbuterol without over reduction of other functional groups.

23. A process as claimed in claim 18, in which the crystals are dried and micronized, the crystallization and drying conditions being selected so as to afford needle-like particles after micronization.

24. A process for the preparation of levalbuterol L-tartrate crystals, which comprises combining a solution of levalbuterol with a solution of L-tartaric acid, recovering levalbuterol L-tartrate crystals, and then drying and micronizing the recovered crystals, the crystallization and drying conditions being selected so as to afford needle-like particles after micronization.

25. Levalbuterol L-tartrate crystals obtained by the process of claim 18.

26. Levalbuterol L-tartrate crystals obtained by the process of claim 24.

27. A method of effecting bronchodilation in a patient in need of treatment, which comprises administering to said patient an effective amount of levalbuterol L-tartrate.

28. A method as claimed in claim 27, in which micronized crystals of levalbuterol L-tartrate are administered by inhalation using a metered dose inhaler.

29. A method as claimed in claim 28, in which the micronized crystals of levalbuterol L-tartrate are in the form of needle-like particles.

* * * * *